(12) United States Patent
Veren (10) Patent No.: US 10,318,710 B2
(45) Date of Patent: Jun. 11, 2019

(54) SYSTEM AND METHOD FOR IDENTIFYING HEALTHCARE FRAUD (71) Applicant: Linda C. Veren, Sudbury, MA (US)

(72) Inventor: Linda C. Veren, Sudbury, MA (US)

( * ) Notice: Subject to any disclaimer, the term of this patent is extended or adjusted under 35 U.S.C. 154(b) by 0 days.

(21) Appl. No.: 13/681,248

(22) Filed: Nov. 19, 2012

(65) Prior Publication Data

US 2014/0129256 A1   May 8, 2014

Related U.S. Application Data

(63) Continuation of application No. PCT/US2012/064246, filed on Nov. 8, 2012.

(60) Provisional application No. 61/557,261, filed on Nov. 8, 2011.

(51) Int. Cl.
*G06Q 40/00* (2012.01)
*G06F 19/00* (2018.01)

(52) U.S. Cl.
CPC ................. *G06F 19/328* (2013.01)

(58) Field of Classification Search
CPC ................ G06F 19/328; G06Q 40/08
USPC ........................................... 705/2–4
See application file for complete search history.

(56) References Cited

U.S. PATENT DOCUMENTS

| | | | |
|---|---|---|---|
| 6,826,536 B1* | 11/2004 | Forman | 705/4 |
| 7,418,431 B1* | 8/2008 | Nies | G06F 16/972 706/21 |
| 2002/0133721 A1 | 9/2002 | Adjaoute | |
| 2003/0135397 A1 | 7/2003 | Halow et al. | |
| 2003/0158751 A1 | 8/2003 | Suresh et al. | |
| 2003/0229519 A1 | 12/2003 | Eidex et al. | |
| 2007/0168232 A1 | 7/2007 | Kimmel | |
| 2007/0219824 A1 | 9/2007 | Rawlings et al. | |
| 2008/0052117 A1 | 2/2008 | Beraja et al. | |
| 2010/0179838 A1 | 7/2010 | Basant et al. | |
| 2014/0058763 A1* | 2/2014 | Zizzamia et al. | 705/4 |

* cited by examiner

*Primary Examiner* — Joseph Burgess
(74) *Attorney, Agent, or Firm* — FisherBroyles, LLP; Ariel Reinitz (57) ABSTRACT

In general, one aspect of the subject matter described herein can be embodied in methods that include the actions of: identifying one or more claims associated with a patient, selecting, from the identified claims at least a first claim and a second claim, comparing one or more patient claim parameters of the first claim with one or more patient claim parameters of the second claim, determining, based on the comparing, one or more patient variables, the one or more patient variables reflecting one or more aspects of the one or more claims associated with the patient, processing the respective determined patient variables to identify one or more patient clusters, each of the one or more patient clusters including one or more claims having one or more substantially similar patient variables, and, providing, based on the one or more identified patient clusters, notifications with respect to a medical entity record.

20 Claims, 3 Drawing Sheets

SYSTEM AND METHOD FOR IDENTIFYING HEALTHCARE FRAUD

CROSS-REFERENCE TO RELATED APPLICATIONS

This application is a continuation application of International PCT Application No. PCT/US12/64246, filed Nov. 8, 2012 which claims the benefit of U.S. Patent Application Ser. No. 61/557,261, filed Nov. 8, 2011, which are hereby incorporated by reference in their entireties.

BACKGROUND

It has been observed that health care fraud is a growing problem. Specifically, fraudulent entities can be created, and substantial numbers of claims can be submitted by such entities. Upon receiving one or more initial payments, such entities can quickly cease operations, substantially before current fraud detection methods are capable of determining that the submitted claims are fraudulent. It is with respect to these and other considerations that the disclosure made herein is presented.

SUMMARY

This specification describes technologies relating to fraud identification.

In general, one aspect of the subject matter described in this specification can be embodied in methods for fraud identification. The method includes the actions of: for each medical entity record, the medical entity record including a set of one or more claims associated with a particular medical entity, each of the one or more claims being associated with (a) a particular patient, (b) a particular provider, and (c) a particular date: for each patient associated with at least one of the one or more claims associated with the medical entity: identifying one or more claims associated with the patient, each of the one or more claims being associated with (a) a particular provider and (b) a particular date, selecting, from the one or more claims associated with the patient, at least (a) a first claim and (b) a second claim, each of the first claim and the second claim having one or more respective patient claim parameters, comparing, with one or more processors executing code, one or more patient claim parameters of the first claim with one or more patient claim parameters of the second claim, and determining, based on the comparing, one or more patient variables, the one or more patient variables reflecting one or more aspects of the one or more claims associated with the patient, processing the respective determined patient variables to identify one or more patient clusters, each of the one or more patient clusters including one or more claims having one or more substantially similar patient variables, and, providing, based on the one or more identified patient clusters, one or more notifications with respect to the medical entity record.

The details of one or more implementations are set forth in the accompanying drawings and the description below. Other features and advantages will be apparent from the description and drawings, and from the claims.

BRIEF DESCRIPTION OF THE DRAWINGS

FIGS. 2A-B depict a first view of depicts a first view of an integrated gaming piece;

Like reference symbols in the various drawings indicate like elements.

DETAILED DESCRIPTION

In certain implementations, the systems and methods described herein encompass a systemic approach to identifying criminally fraudulent medical claims (i.e., claims for reimbursement for services provided). The described technologies can incorporate the use of social networking and aggregated episode of care attributes/variables/parameters for each patient, and can be independent of specific disease treatment paths or statistics over a health care dataset (such as a datatset pertaining to a medical entity, e.g., a medical practice, hospital, etc.). Moreover, in certain implementations, in lieu of calculating pertinent statistics, variables, etc., over an entire health care dataset, such items can be computed with respect to an individual medical entity/provider and its associated claims to identify suspicion of fraud. In doing so, a fraudulent medical entity/provider can be identified based on a relatively small number of initial instances (e.g., within the first couple of days of billing activity). Moreover, in certain implementations, historical billing information (if available for a medical entity/provider) can be used to further improve the various determinations.

Accordingly, described herein are systems and methods for fraud identification. The referenced systems and methods are now described more fully with reference to the accompanying drawings, in which one or more illustrated embodiments and/or arrangements of the systems and methods are shown. The systems and methods are not limited in any way to the illustrated embodiments and/or arrangements as the illustrated embodiments and/or arrangements described below are merely exemplary of the systems and methods, which can be embodied in various forms, as appreciated by one skilled in the art. Therefore, it is to be understood that any structural and functional details disclosed herein are not to be interpreted as limiting the systems and methods, but rather are provided as a representative embodiment and/or arrangement for teaching one skilled in the art one or more ways to implement the systems and methods. Accordingly, aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Furthermore, the terms and phrases used herein are not intended to be limiting, but rather are to provide an understandable description of the systems and methods.

Figure 1:
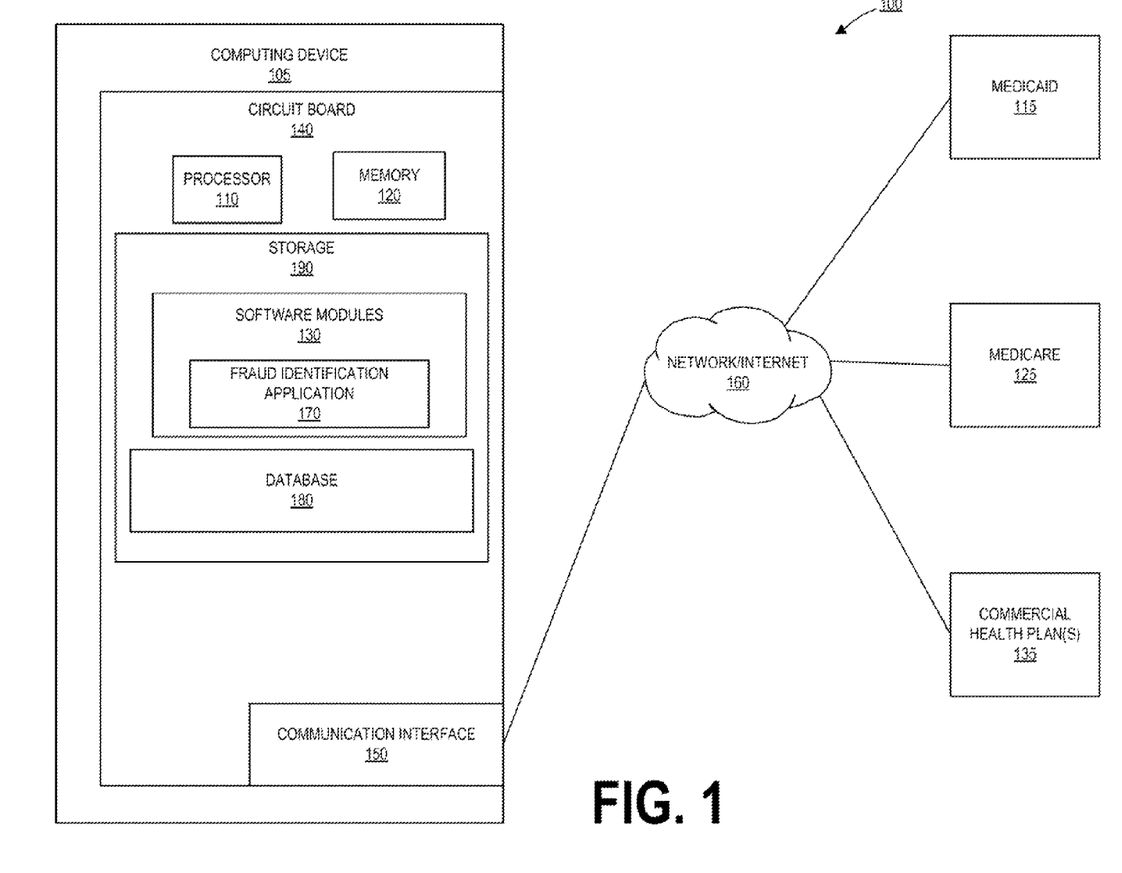
FIG. 1 is a high-level diagram illustrating an exemplary configuration of a fraud identification system.

An exemplary computer system is shown as a block diagram in FIG. 1 which is a high-level diagram illustrating an exemplary configuration of a fraud identification system 100. In one implementation, computing device 105 can be a personal computer or server. In other implementations, computing device 105 can be a tablet computer, a laptop computer, or a mobile device/smartphone, though it should be understood that computing device 105 of fraud identification system 100 can be practically any computing device and/or data processing apparatus capable of embodying the systems and/or methods described herein.

Computing device 105 of fraud identification system 100 includes a circuit board 140, such as a motherboard, which is operatively connected to various hardware and software components that serve to enable operation of the fraud identification system 100. The circuit board 140 is operatively connected to a processor 110 and a memory 120. Processor 110 serves to execute instructions for software that can be loaded into memory 120. Processor 110 can be a number of processors, a multi-processor core, or some other type of processor, depending on the particular implementation. Further, processor 110 can be implemented using a number of heterogeneous processor systems in which a main processor is present with secondary processors on a single chip. As another illustrative example, processor 110 can be a symmetric multi-processor system containing multiple processors of the same type.

Preferably, memory 120 and/or storage 190 are accessible by processor 110, thereby enabling processor 110 to receive and execute instructions stored on memory 120 and/or on storage 190. Memory 120 can be, for example, a random access memory (RAM) or any other suitable volatile or non-volatile computer readable storage medium. In addition, memory 120 can be fixed or removable. Storage 190 can take various forms, depending on the particular implementation. For example, storage 190 can contain one or more components or devices such as a hard drive, a flash memory, a rewritable optical disk, a rewritable magnetic tape, or some combination of the above. Storage 190 also can be fixed or removable.

One or more software modules 130 are encoded in storage 190 and/or in memory 120. The software modules 130 can comprise one or more software programs or applications having computer program code or a set of instructions executed in processor 110. Such computer program code or instructions for carrying out operations for aspects of the systems and methods disclosed herein can be written in any combination of one or more programming languages, including an object oriented programming language such as Java, Smalltalk, C++, Python, and JavaScript or the like and conventional procedural programming languages, such as the "C" programming language or similar programming languages. The program code can execute entirely on computing device 105, partly on computing device 105, as a stand-alone software package, partly on computing device 105 and partly on a remote computer/device, or entirely on the remote computer/device or server. In the latter scenario, the remote computer can be connected to computing device 105 through any type of network, including a local area network (LAN) or a wide area network (WAN), or the connection can be made to an external computer (for example, through the Internet 160 using an Internet Service Provider).

One or more software modules 130, including program code/instructions, are located in a functional form on one or more computer readable storage devices (such as memory 120 and/or storage 190) that can be selectively removable. The software modules 130 can be loaded onto or transferred to computing device 105 for execution by processor 110. It can also be said that the program code of software modules 130 and one or more computer readable storage devices (such as memory 120 and/or storage 190) form a computer program product that can be manufactured and/or distributed in accordance with the present invention, as is known to those of ordinary skill in the art.

It should be understood that in some illustrative embodiments, one or more of software modules 130 can be downloaded over a network to storage 190 from another device or system via communication interface 150 for use within fraud identification system 100. For instance, program code stored in a computer readable storage device in a server can be downloaded over a network from the server to fraud identification system 100.

Preferably, included among the software modules 130 is a fraud identification application 170 that is executed by processor 110. During execution of the software modules 130, and specifically the fraud identification application 170, the processor 110 configures the circuit board 140 to perform various operations relating to fraud identification with computing device 105, as will be described in greater detail below. It should be understood that while software modules 130 and/or fraud identification application 170 can be embodied in any number of computer executable formats, in certain implementations software modules 130 and/or fraud identification application 170 comprise one or more applications that are configured to be executed at computing device 105 in conjunction with one or more applications or 'apps' executing at remote devices, such as computing device(s) 115, 125, and/or 135 and/or one or more viewers such as internet browsers and/or proprietary applications. Furthermore, in certain implementations, software modules 130 and/or fraud identification application 170 can be configured to execute at the request or selection of a user of one of computing devices 115, 125, and/or 135 (or any other such user having the ability to execute a program in relation to computing device 105, such as a network administrator), while in other implementations computing device 105 can be configured to automatically execute software modules 130 and/or fraud identification application 170, without requiring an affirmative request to execute. Tt should also be noted that while FIG. 1 depicts memory 120 oriented on circuit board 140, in an alternate arrangement, memory 120 can be operatively connected to the circuit board 140. In addition, it should be noted that other information and/or data relevant to the operation of the present systems and methods (such as database 180) can also be stored on storage 190, as will be discussed in greater detail below.

Also preferably stored on storage 190 is database 180. As will be described in greater detail below, database 180 contains and/or maintains various data items and elements that are utilized throughout the various operations of fraud identification system 100, as will be described in greater detail herein. It should be noted that although database 180 is depicted as being configured locally to computing device 105, in certain implementations database 180 and/or various of the data elements stored therein can be located remotely (such as on a remote device or server—not shown) and connected to computing device 105 through network 160, in a manner known to those of ordinary skill in the art.

As referenced above, it should be noted that in certain implementations, such as the one depicted in FIG. 1, various of the computing devices 115, 125, 135 can be in periodic or ongoing communication with computing device 105 thorough a computer network such as the Internet 160. Though not shown, it should be understood that in certain other implementations, computing devices 115, 125, and/or 135 can be in periodic or ongoing direct communication with computing device 105, such as through communications interface 150, such as during an interactive multiplayer game. For example, as depicted in FIG. 1, computing device 115 can correspond to a computing device containing data from Medicaid, while computing device 125 can correspond to a computing device containing data from Medicare, and computing device 135 can correspond to a computing device containing data from a commercial health plan, each of which can be in communication with computing device 105 as described in detail herein.

Communication interface 150 is also operatively connected to circuit board 140. Communication interface 150 can be any interface that enables communication between the computing device 105 and external devices, machines and/or elements. Preferably, communication interface 150 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting computing device 105 to other computing devices and/or communication networks such as private networks and the Internet. Such connections can include a wired connection or a wireless connection (e.g. using the 802.11 standard) though it should be understood that communication interface 150 can be practically any interface that enables communication to/from the circuit board 140.

As noted above, at various points during the operation of fraud identification system 100, computing device 105 can communicate with one or more computing devices, such as those controlled and/or maintained by one or more individuals and/or entities, such as user devices 115, 125, and/or 135. Such computing devices transmit and/or receive data to/from computing device 105, thereby preferably initiating maintaining, and/or enhancing the operation of the fraud identification system 100, as will be described in greater detail below. It should be understood that the computing devices 115-135 can be in direct communication with computing device 105, indirect communication with computing device 105, and/or can be communicatively coordinated with computing device 105, as will be described in greater detail below. While such computing devices can be practically any device capable of communication with computing device 105, in certain embodiments various of the computing devices are preferably servers, while other computing devices are preferably user devices (e.g., personal computers, handheld/portable computers, smartphones, etc.), though it should be understood that practically any computing device that is capable of transmitting and/or receiving data to/from computing device 105 can be similarly substituted.

It should be noted that while FIG. 1 depicts fraud identification system 100 with respect to computing devices 115, 125, and 135, it should be understood that any number of computing devices can interact with the fraud identification system 100 in the manner described herein. It should be further understood that a substantial number of the operations described herein are initiated by and/or performed in relation to such computing devices. For example, as referenced above, such computing devices can execute applications and/or viewers which request and/or receive data from computing device 105, such as in order to identify fraud within their own programs, substantially in the manner described in detail herein.

In the description that follows, certain embodiments and/or arrangements are described with reference to acts and symbolic representations of operations that are performed by one or more devices, such as the fraud identification system 100 of FIG. 1. As such, it will be understood that such acts and operations, which are at times referred to as being computer-executed or computer-implemented, include the manipulation by processor 110 of electrical signals representing data in a structured form. This manipulation transforms the data and/or maintains them at locations in the memory system of the computer (such as memory 120 and/or storage 190), which reconfigures and/or otherwise alters the operation of the system in a manner understood by those skilled in the art. The data structures in which data are maintained are physical locations of the memory that have particular properties defined by the format of the data. However, while an embodiment is being described in the foregoing context, it is not meant to provide architectural limitations to the manner in which different embodiments can be implemented. The different illustrative embodiments can be implemented in a system including components in addition to or in place of those illustrated for the fraud identification system 100. Other components shown in FIG. 1 can be varied from the illustrative examples shown. The different embodiments can be implemented using any hardware device or system capable of running program code. In another illustrative example, fraud identification system 100 can take the form of a hardware unit that has circuits that are manufactured or configured for a particular use. This type of hardware can perform operations without needing program code to be loaded into a memory from a computer readable storage device to be configured to perform the operations.

For example, computing device 105 can take the form of a circuit system, an application specific integrated circuit (ASIC), a programmable logic device, or some other suitable type of hardware configured to perform a number of operations. With a programmable logic device, the device is configured to perform the number of operations. The device can be reconfigured at a later time or can be permanently configured to perform the number of operations. Examples of programmable logic devices include, for example, a programmable logic array, programmable array logic, a field programmable logic array, a field programmable gate array, and other suitable hardware devices. With this type of implementation, software modules 130 can be omitted because the processes for the different embodiments are implemented in a hardware unit.

In still another illustrative example, computing device 105 can be implemented using a combination of processors found hi computers and hardware units. Processor 110 can have a number of hardware units and a number of processors that are configured to execute software modules 130. In this example, some of the processors can be implemented in the number of hardware units, while other processors can be implemented in the number of processors.

In another example, a bus system can be implemented and can be comprised of one or more buses, such as a system bus or an input/output bus. Of course, the bus system can be implemented using any suitable type of architecture that provides for a transfer of data between different components or devices attached to the bus system. Additionally, communications interface 150 can include one or more devices used to transmit and receive data, such as a modem or a network adapter.

Embodiments and/or arrangements can be described in a general context of computer-executable instructions, such as program modules, being executed by a computer. Generally, program modules include routines, programs, objects, components, data structures, etc., that perform particular tasks or implement particular abstract data types.

It should be further understood that while the various computing devices and machines referenced herein, including but not limited to computing device 105, computing devices 115, 125, and 135 are referred to herein as individual/single devices and/or machines, in certain implementations the referenced devices and machines, and their associated and/or accompanying operations, features, and/or functionalities can be arranged or otherwise employed across any number of devices and/or machines, such as over a network connection, as is known to those of skill in the art. It should also be noted that, although not all shown in FIG. 1, various additional components can be incorporated within and/or employed in conjunction with computing device 105.

It has been observed that fraudulent medical entities, such as pharmacies, durable medical equipment (DME) providers, long term care facilities, nursing homes and physician practices are being established by criminal enterprises in states across the US. These criminal enterprises purchase lists of individual medical identification numbers for patients and doctors and use them to bill for nonexistent medical equipment, medical procedures, and prescriptions. Such fraudulent entities bill the health care system at a high rate over a period of a few of weeks or months and then close. Generally, by the time the fraud has been identified, the entity has stopped billing and disappeared and the stolen funds cannot be recovered. For example, a single medical entity could bill for millions of dollars within a 2 month period.

Generally, the claims submitted by such fictional practices, pharmacies, DMEs, etc. are on behalf of fictional patients that are not actually being treated at all. Such entities are often incapable of duplicating the complexity and diversity of disease states that any practice, pharmacy or DME should exhibit over the breadth of their (legitimate) patient claims. For example, patients do not always follow the directives provided by a health care provider. Additionally, the manner in which different doctors treat diseases can vary by specialty and geographic region. Patients can also have different combinations of co-morbidities and behave differently depending on their medical insurance coverage and age. Accordingly, most fraudulent attempts to create fictional treatment paths for a large set of patients tend to show certain measures or aspects of similarity that are generally not otherwise present in legitimate health care claims.

Moreover, techniques employed successfully in such fraudulent medical practices, etc. in one geographic area are generally subsequently attempted in other geographic areas. For example, when a scheme is successful in one location, it will generally be repeated elsewhere, whether within the same region or in a different one. Accordingly, as described herein, an analysis of various social networking factors (which enable the identification of unique users across multiple data sets) and parameters and variables associated with various health care related claims can indicate the probability that a set of medical identification records (corresponding to a number of patients) is been shared among several fraudulent medical entities.

In certain implementations, the systems and methods described herein can encompass a health care entity patient population classification system that can identify when a medical entity is using illegally obtained medical identification numbers for patients and/or illegally obtained physician/provider identification numbers. Moreover, in certain implementations, the described technologies can be fully automated and require no analyst intervention in order to identify fraudulent activity. Additionally, as described herein, machine learning techniques can be incorporated such that the system can 'learn' over time as more data is gathered on different schemes (e.g., with respect to different parts of the country and/or medical entity types). In doing so, payment claims for such entities/providers can be flagged as potentially fraudulent and payment for such claims can be delayed, denied or audited accordingly. Additionally, in certain implementations an individual patient profile can be created. Such a profile can incorporate a user's social networking information together with his/her episode of care summary attributes. Such individual patient profiles can be analyzed to compute a medical entity/provider profile for a particular medical entity or entities (e.g., a physician, pharmacy or DME). Each medical entity and/or provider can be assigned a rating or score indicating the probability/likelihood that they are using illegally obtained medical identification information and/or are filing false claims. Moreover, the profiles of the potentially fraudulent medical entities can be stored in a library that can be used further refine and improve the accuracy of the system, as described herein.

In certain implementations, and as described in greater detail herein, a claim such as a first or most recent claim, such as a pharmaceutical (Rx) claim or a medical (Mx) claim for a particular patient or patients, can be identified, such as with respect to a new medical entity/provider. In doing so, a most recent prior medical, DME or pharmacy claim can be identified with respect to a particular patient, and a profile of characteristics/parameters of the current and most recent prior claim can be developed. Examples of such characteristics/parameters include, but are not limited to: elapsed time to most recent prior claim, geographic location of treatment, patient demographics including gender, age and home geographic information, physician DEA number, name and specialty, diagnosis, claim type (prescription, medical, DME), for prescription claim record: pharmaceutical name, drug class, days supply and/or quantity dispensed, for DME claim record: the medical equipment name and class, for medical claim record: the ICD9 or CPT code information, health insurer, and/or payment channel, though it should be understood that any number of other parameters are similarly contemplated and are within the scope of the systems and methods described herein.

It should be noted that, in certain scenarios, a particular medical data set or sets (e.g., a data set corresponding to a particular health care provider such as a pharmacy or physician) may not contain the most recent prior patient claim for all current patients (e.g., a patient may have switched health plans or gone on vacation). Accordingly, in certain implementations information from other medical data sets can also be processed/analyzed in order to consider more of or all medical claim information available with regard to a particular patient. In doing so, a set of attributes/variables can be computed for a patient based on some or all of their available claims, billed by a medical entity, within various time periods or timeframes (e.g., beginning from a first documented claim and going forward and/or backward for the specified time duration). Examples of such time periods include, but are not limited to: 1 day, 2 days, 3 days, 4 days, 5 days, 6 days, 4 weeks, 3 months, 6 months, 12 months, 18 months, and/or 24 months, though other timeframes are similarly contemplated.

Additionally, the various sets of attributes/variables, such as those calculated over various time periods (e.g., backwards and/or forwards in time from the first time that a claim is submitted for payment by a medical entity) can be added to the individual patient profile. These attributes can include, but are not limited to: the number of physicians seen (e.g., segmented by specialty), the number of different prescriptions filled (e.g., segmented by pharmaceutical drug class, prescription name and/or type, such as mail-order versus non mail-order), compliance and persistency calculations for all prescriptions segmented by drug class and prescription name, the number of titration episodes for prescriptions (e.g., segmented by drug class and prescription name), the number of DME claims (e.g., segmented by equipment class), the number of medical claims (e.g., segmented by disease class and claim type, such as office visit, procedure, blood test etc.), the number of diseases diagnosed (e.g., segmented by disease class), the number of episodes of medical care (e.g., as defined as periods of billing versus periods of 3 months with no medical and/or prescription activity), the number of health insurers (e.g., segmented by health insurance type), the number of different types of claim payment channels by patient (e.g., cash, Medicare/Medicaid, private insurance etc.), and/or the number of total claims (e.g., segmented by zip code) associated with treatment or prescription.

Moreover, a profile can be generated for each medical entity/provider, such as based on the statistics of their aggregated patient profile information. Such a profile can include variables that, in turn, reflect a combination of various variables that are calculated over different time periods. Such time periods can include, for example: 1) the time between the first claim for a medical entity within the dataset and the most previous (e.g., the first) claim, 2) the first claim date for a medical entity and looking back in time, and/or 3) the first claim date for a medical entity and looking forward in time. Statistics, including minimum, maximum, range, mean, median, standard deviation and standard deviation/mean can be calculated at the medical entity level for any/all aggregated patient characteristics.

In scenarios where the medical entity being profiled is not a physician or physician group, an additional layer of analysis can be implemented. Such an approach can build a profile (e.g., variables as described herein) for each physician within the particular medical entity. A profile can then be computed for the medical entity as a whole, taking into account the aggregated physician findings. It should also be noted that, in scenarios where multiple time periods are used in, multiple profiles can be generated for each patient, physician, medical entity, etc., one profile for each time period. It can be appreciated that the presence of fraud may be undetectable (or more difficult to identify) with respect to one time period (e.g., a week or a month) while such fraud may be more easily detected over another time period (e.g., six months or one year).

The various claims that are analyzed as part of a particular lookback period (e.g., from the date of the first claim for a medical entity) can access or 'pull' data regarding a particular patient that is stored across multiple databases (e.g., those stored at 115, 125, and/or 135), such as those maintained by various health insurance companies.

Moreover, in many scenarios where claims are submitted by a medical entity in relation to patients that are not actually receiving the billed-for services, data (e.g., parameters, variables, etc.) corresponding to such claims can demonstrate similar characteristics, such as at the physician or medical entity level. Techniques such as clustering (as are known to those of ordinary skill in the art), which identify similarities between entities by analyzing sets of attributes for an entity, can be employed, based upon which similar types of behaviors can be identified for a patient, physician, and/or medical entity, such as with respect to multiple patients. It can be appreciated that authentic, non-fraudulent data generated from patients who are actually being treated for medical conditions is likely to exhibit randomness across the patient group (e.g., all patients do not respond to drugs in the same way and are generally not as willing to undergo extensive testing). Accordingly, various parameters/variables corresponding to such authentic, non-fraudulent data are unlikely to 'cluster' over a group of patients. The employed clustering techniques can identify fraudulent patient data patterns (e.g., a high likelihood of fraud can be identified if the data for multiple patients clusters into one group). By way of further illustration, if part of a medical practice is authentic and another part of the practice is fraudulent, the data will cluster into two groups (or only a subset of the data may cluster, while the rest may not).

It should be noted that while clustering techniques are one way to identify the referenced patterns, in other implementations standard deviation/mean calculations for individual patient variables can be used to determine a "closeness" factor for the patient's behavior.

Additionally, in certain implementations, various binary (e.g., YES/NO) attributes/variables can be measured as a part of the patient level and/or the medical entity aggregate variables. Examples of such binary attributes can include, but are not limited to: if two different claims (e.g., a first claim in the dataset for a medical entity with respect to a particular patient and the most recent claim by that same patient across all medical entities) share the same physician, or whether the two claims are for the same prescription drug. These variable types can be used to refine the approach used over time. Using nearest neighbor retrieval techniques, as are known to those of ordinary skill in the art, the medical entity/provider profiles can be compared in order to measure their correlation factor for suspiciousness/likelihood of fraud. In certain implementations, a level of suspicion can be determined based on clustering and the "closeness" factor determined by aggregate variables' standard deviation/mean. As the library of medical entity profiles becomes larger, the referenced techniques can be refined to account for this second type of variable (examples of such variables can be numeric variables and binary variables). Additionally, the recovery type (e.g., before payment or after payment), recovered claim costs, and recovery time can be added to the library profile for each entity.

Upon implementing the technologies described herein, in certain implementations, upon receiving new data (e.g., corresponding to subsequent medical claims), the techniques described herein need only be employed with respect to the newly received data (or the data that has become available since a previous processing instance). In doing so, the supporting database can store individual patient aggregate information before statistics are applied. Accordingly, in certain implementations, for each physician/provider, the database can store the patient list, and claim range date for each patient, that has billed claims by the physician. This patient list can be checked as new claims come into the dataset to determine if the physician profile needs to be recomputed. As noted above, if the majority of patients within a medical entity share a similar profile, such a pattern can indicate that these patients are not actually real patients, and that these treatments are actually fraudulent.

For example, if a new pharmacy in Illinois starts billing for 100 patients at the start of the year and all 100 of these patients last filed a claim 85 days prior in California, such activity can be determined to be suspicious and can indicate potential medical identification theft and sharing of patient lists. Or, if a new DME starts billing for 500 patients and the majority of these patients had a high persistency and compliance for all their prescriptions over the past 12 months, this could indicate a high likelihood of fraud. As noted above, a normal population of actual patients is likely to have a range of persistency and compliance over the set of their prescription usage over time. It should be noted, however, that the foregoing examples are merely illustrative, and that any number of other types of activity can be identified as indicative of fraud, as identified in the manner described herein.

By way of illustration, by determining the "closeness" factor present in the medical billing behavior of the patients of a particular medical provider over time, it can be determined if the particular provider's practice is fraudulent and does not actually exist. Such an exemplary process can include the following operations:

Identify the list of patients that have submitted a claim within the health care claims dataset for payment where the particular medical provider (e.g., Dr. Smith) is the physician.

Identify the first date for each patient of Dr. Smith's when they first submitted an Rx and/or an Mx health care claim for payment.

Determine if Dr. Smith is a new provider that is submitting claims for payments in this health care set. (If Dr. Smith has just submitted claims for one day then he will have no history of claims in this dataset.)

For each of Dr. Smith's patients that have submitted claims, identify the most recent prior Rx and/or Mx claim that those patients made in relation to another provider. (For some patients, there may not be a prior claim.)

For each patient of Dr. Smith, calculate a set of attributes/variables from comparison of the set of the first claim submitted for Dr. Smith and the most recent claim submitted under another provider (e.g., a comparison of the respective parameters of each claim). An example of these attributes/parameters is the exact identification of the prescription drug prescribed on the Rx claims. Another example is the difference in miles in the geography of the two doctors practices. One important attribute is the length of time between those two claims in time. For doctors who are using patient lists composed of deceased patients, there may be no prior record for any of his patients in this dataset or, conversely, all of them may show up as billing previously at the same exact time for the same doctor.

For each patient of Dr. Smith who has more than one day of claims submitted in this health care dataset, their first claim submitted has been identified. From that date, identify all claims that have been submitted for payment in this dataset for all providers (i.e., not just Dr. Smith) for a given time period after this initial claim date (e.g., up to 2 years in length). Using this set of claims (which are all for all providers), calculate patient level attributes/parameters/variables, such as including the number of different Rxs submitted, the number of different diagnosis submitted on Mx claims and/or the number of primary care physicians that the patient has been billed under. It is important to note that these attributes are calculated for the set of Dr. Smith's patients, but over the entire dataset for all providers and medical entities that Dr. Smith's patients have billed under.

For Dr. Smith, take the two different sets of attributes calculated above and calculate statistics for Dr. Smith's patients as a group. If Dr. Smith's patients are exhibit extremely close behavior without natural variation then the suspicion is that he is not treating these patients for a disease but instead this is a fraudulent practice. For each attribute (e.g., a numerical attribute), calculate the standard deviation/average to give a measure of the "closeness" of Dr. Smith's patients for each individual variable measured. The addition of all of these statistics for the set of attributes for Dr. Smith's patient group can be used to rank Dr. Smith versus the other medical entities in the health care dataset. For example, a low value is more suspicious. For instance, if all of Dr. Smith's patients submit the same 4 Rxs for depression, every 30 days for an entire year that would be an abnormal prescribing pattern to happen. Patients have different tolerance levels for different drugs and also the efficacy of drugs is different between people. In legitimate, non-fraudulent situations, there should almost always be variation over a set of patients for a single physician over time. For Dr. Smith, the average number of Rxs for each patient would be 120, with a standard deviation of zero. The number of different Rxs for each patient would be 4 with a standard deviation of zero. The persistency of each of Dr. Smith's patients would be 100% with a standard deviation of zero. If those were the four total attributes being calculated for Dr. Smith he would have a "closeness" score of zero. In this example, the Dr. Smith's patients only had claims that were billed under Dr. Smith and no other provider.

After the entire health care data set is ranked according to the two approaches defined above, the entities are ordered according to their total "closeness" score relative to the number of attributes that are measured for the individual provider. A low score is more suspicious but must be normalized for the set of attributes that has contributed to the score. The lowest scores must be considered against the total dollar amount being billed to determine which cases will give the highest return on investment for investigation of suspected fraud The operation of the fraud identification system 100 and the various elements and components described above will be further appreciated with reference to the method for fraud identification as described herein.

Figure 2A:
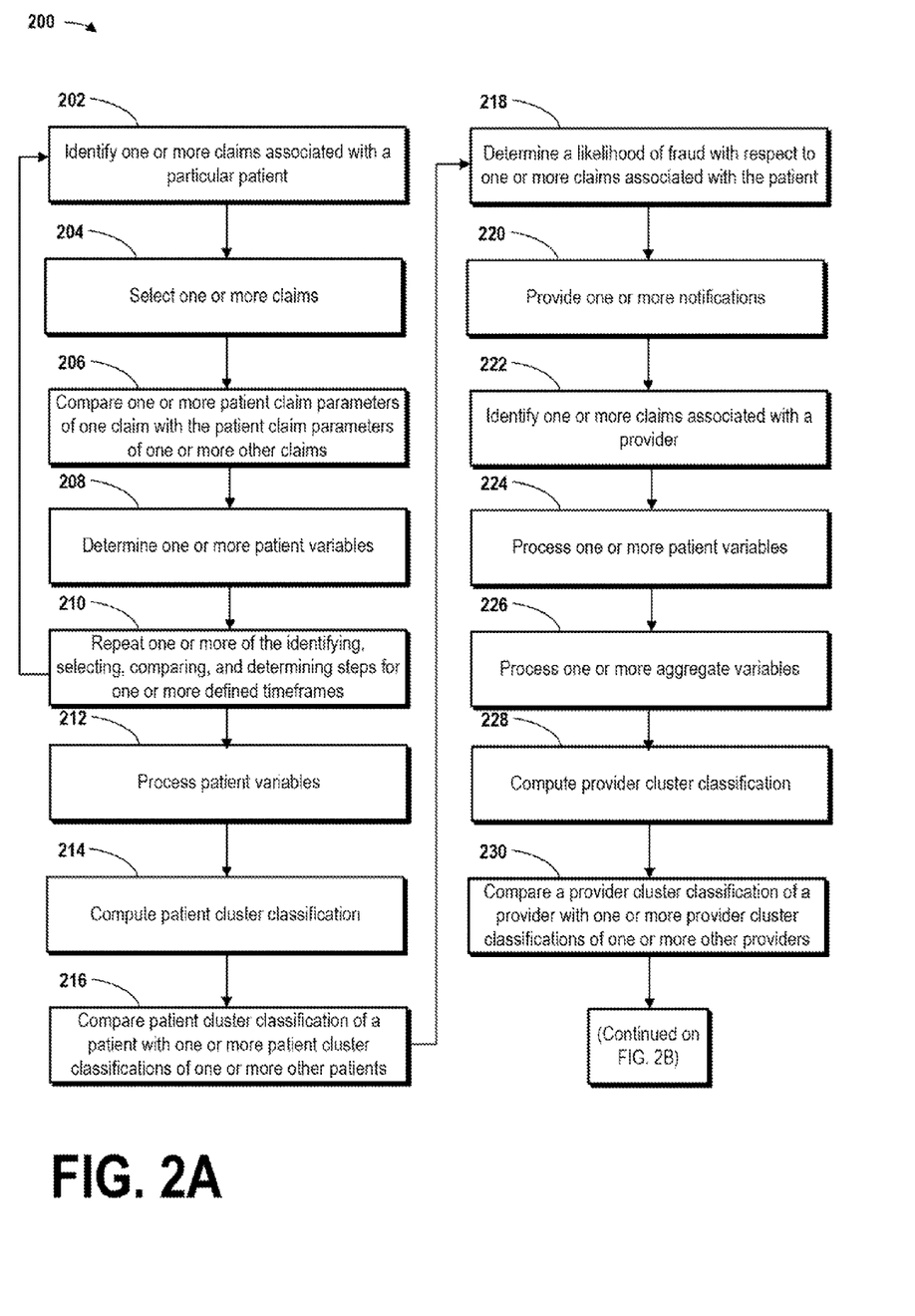
Figure 2B:
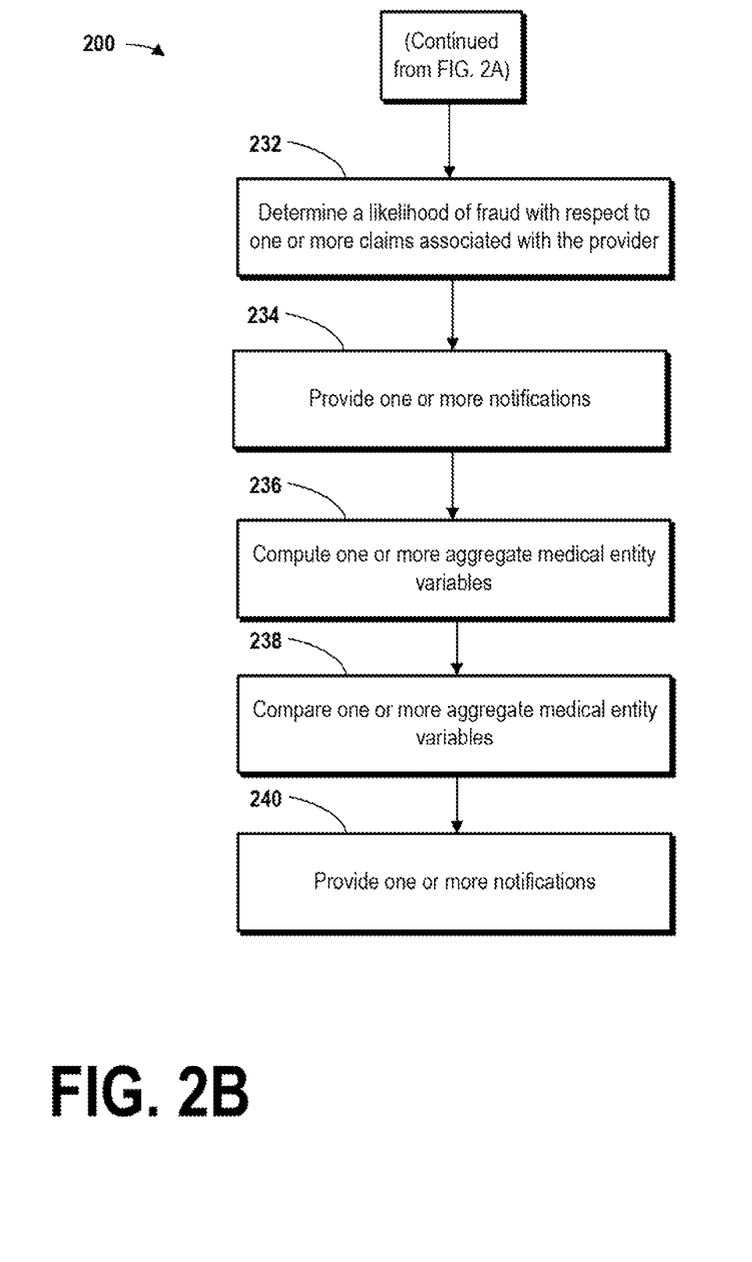
FIG. 2B depict flow diagrams showing a routine that illustrates a broad aspect of a method for fraud identification in accordance with at least one embodiment disclosed herein.

Turning now to FIGS. 2A-2B, a flow diagram is described showing a routine 200 that illustrates a broad aspect of a method for fraud identification in accordance with at least one embodiment disclosed herein. It should be appreciated that several of the logical operations described herein are implemented (1) as a sequence of computer implemented acts or program modules running on fraud identification system 100 and/or (2) as interconnected machine logic circuits or circuit modules within the fraud identification system 100. The implementation is a matter of choice dependent on the requirements of the device (e.g., size, energy, consumption, performance, etc.). Accordingly, the logical operations described herein are referred to variously as operations, steps, structural devices, acts, or modules. As referenced above, various of these operations, steps, structural devices, acts and modules can be implemented in software, in firmware, in special purpose digital logic, and any combination thereof. It should also be appreciated that more or fewer operations can be performed than shown in the figures and described herein. These operations can also be performed in a different order than those described herein.

At 202, processor 110 executing one or more of software modules 130, including, in certain implementations, fraud identification application 170, configures computing device 105 to identify one or more claims associated with a particular patient. In certain implementations, such identifying can be performed with respect to one or more medical entity records, such as records that reflect or correspond to one or more healthcare claims (or any other such claims) that are associated with or otherwise correspond to one or more medical entities. Such records can originate at and/or be compiled from any number of data sources, including but not limited to: Medicaid Health Care Claims, Medicare Health Care Claims, Other Government Health Care Claims, and/or Commercial Health Plan Claims, though such sources are merely illustrative, and any number of other sources are similarly contemplated. Such medical entity records can include a set of one or more claims, such as claims associated with a particular medical entity. Moreover, each of the referenced claims can be associated with (a) a particular patient, (b) a particular provider, and (c) a particular date. In certain implementations, a unique identifier (ID) can be assigned to each unique patient and/or provider, as well as to each claim, and such an ID can be employed across any number of datasets. Additionally, in certain implementations, the referenced identifying can be performed (such as in an automated or automatic fashion) for one or more patients that are associated with one or more of the one or more claims that are associated with the medical entity.

At this juncture, it should be noted that 'medical entity,' as used herein, can include, but is not limited to entities such as: Insurance company, Physician, Physician Group, Nurse Practitioner, Physician Assistant, Pharmacy, Mail Order Pharmacy, Specialty Pharmacy, Durable Medical Equipment Provider, Vascular Clinic, Dialysis Clinic, Mental Health Clinic, Long Term Care Facility, Nursing Home, and/or Transportation Company.

At 204, processor 110 executing one or more of software modules 130, including, in certain implementations, fraud identification application 170, configures computing device 105 to select one or more claims. In certain implementations, such claims can be selected from the one or more claims identified at 202 as being associated with a particular patient. Additionally, in certain implementations the initially selected claims can be claims that are most recent in time. Moreover, in certain implementations, the referenced selected claims can be chronologically contiguous to one another (e.g., immediately preceding or succeeding one another in time). For example, a first claim and a second claim can be selected, each of which can have one or more respective patient claim parameters/attributes. Examples of such patient claim parameters can include, but are not limited to: Rx Claim ID, Mx Claim ID, most recent Rx Claim ID, most recent Mx Claim ID, Date of Claim, Prescriber, Prescriber Specialty, Diagnosis Codes, Procedure Codes, Lab Tests, NCPDP codes, Rx Drug Class, Rx Drug Name, Rx Drug Quantity Dispensed, Rx Drug Days Supply, Payment Method, Patient Copay, Claim Dollar Cost, Medical entity zip code, Medical entity State Location, Medical Entity Type, etc. By way of further illustration, one claim can correspond to a medical claim while another claim can correspond to a pharmaceutical claim Additionally, in certain implementations, the referenced selecting can be performed (such as in an automated or automatic fashion) with respect to one or more medical entity records and/or for one or more patients that are associated with one or more of the one or more claims that are associated with the medical entity.

At 206, processor 110 executing one or more of software modules 130, including, in certain implementations, fraud identification application 170, configures computing device 105 to compare one or more patient claim parameters of one claim with the patient claim parameters of one or more other claims (such as those selected at 204). In certain implementations, the referenced comparing can be performed (such as in an automated or automatic fashion) with respect to one or more medical entity records and/or for one or more patients that are associated with one or more of the one or more claims that are associated with the medical entity.

At 208, processor 110 executing one or more of software modules 130, including, in certain implementations, fraud identification application 170, configures computing device 105 to determine one or more patient variables. In certain implementations, such patient variables can be determined, based on the comparison of various patient claim parameters at 206. Such patient variables can reflect various aspects of the one or more claims associated with the patient. Examples of such patient variables include, but are not limited to: Number of claim cash payments by patient, Total Cost, Total Patient Payment Cost, Number of Physicians, Number of Physician Specialties, Number of Primary Care Physicians, Number of Rxs, Number of Mail Order Rxs, Number of Pharmacies, Rx persistency by drug and drug class, Rx compliance by drug and drug class, Number of Mxs, Ratio of Rx total to Mx total, Number of rejected Rx claims, Number of rejected Mx claims, Total Timespan, Number of Rx classes, Number of first line Rx drugs, Number of second line Rx drugs, Number of diagnosis, Number of procedures, General line of therapy for Mx body sections, Number of Rx concomitant drugs, Number of dropped Rx drugs, Number of switched Rx drugs, Number of restarted Rx drugs, Number of periods of 3 months or greater of no Rx activity, Number of periods of 3 months or greater of no Mx activity, Number of geographic locations for billing provider; both zip, codes and States, Greatest geographic location difference for billing provider in miles, Number of DME providers, Number of medical equipment claims, Number of different types of medical equipment, Calculate projected costs for patient over next 12 months based on Rx claims in isolation; calculate same figure based on combined Mx and Rx claims; Calculate % difference between the two projections, calculate cost difference between the two projections, etc. Further such examples (including determinations based on an Mx claim and a Rx claim) include: Geographic Distance Calculations, Time Difference Calculations, Patient Copay Difference, Claim Cost Difference, Same Payment Method?, Same Prescriber?, Same Prescriber Specialty?, Same Rx Drug Class?, Same Rx NCPDP code?, Rx Days Supply Difference, Rx Quantity Dispensed Difference, Same Mx Diagnosis?, Same Mx Diagnosis Group?, Same Procedure?, Same Procedure Group?, Both Acute Conditions?, Both Chronic Conditions? Moreover, in certain implementations, the referenced determining can be performed (such as in an automated or automatic fashion) with respect to one or more medical entity records and/or for one or more patients that are associated with one or more of the one or more claims that are associated with the medical entity.

At 210, processor 110 executing one or more of software modules 130, including, in certain implementations, fraud identification application 170, configures computing device 105 to repeat one or more of the identifying (202), selecting (204), comparing (206), and determining (208) steps for one or more defined timeframes. That is, it should be appreciated that the referenced claims, such as those identified at 202, can correspond to one or more claims associated with a particular patient that occur within a defined timeframe, such as the timeframes referenced herein. In certain implementations, the referenced repeating can be performed (such as in an automated or automatic fashion) with respect to one or more medical entity records and/or for one or more patients that are associated with one or more of the one or more claims that are associated with the medical entity.

At 212, processor 110 executing one or more of software modules 130, including, in certain implementations, fraud identification application 170, configures computing device 105 to process various patient variables (such as those determined at 208). In doing so, one or more patient clusters can be identified. In certain implementations, such patient clusters can include various claims that have one or more substantially similar patient variables. Moreover, in certain implementations, the referenced processing can be performed (such as in an automated or automatic fashion) with respect to one or more medical entity records.

At 214, processor 110 executing one or more of software modules 130, including, in certain implementations, fraud identification application 170, configures computing device 105 to compute a patient cluster classification with respect to the patient, reflecting, for example, the manner in which various variables associated with the patient cluster. In certain implementations, such as a patient cluster classification can be computed based on one or more patient clusters, such as those identified at 212. Additionally, in certain implementations, the referenced computing can be performed (such as in an automated or automatic fashion) with respect to one or more medical entity records and/or for one or more patients that are associated with one or more of the one or more claims that are associated with the medical entity.

At 216, processor 110 executing one or more of software modules 130, including, in certain implementations, fraud identification application 170, configures computing device 105 to compare a patient cluster classification of the patient (such as that computed at 214) with one or more patient cluster classifications of one or more other patients. In doing so, one or more patients that have a comparable patient cluster classification to the patient can be identified. In certain implementations, the referenced comparing can be performed (such as in an automated or automatic fashion) with respect to one or more medical entity records and/or for one or more patients that are associated with one or more of the one or more claims that are associated with the medical entity.

At 218, processor 110 executing one or more of software modules 130, including, in certain implementations, fraud identification application 170, configures computing device 105 to determine a likelihood of fraud with respect to one or more claims associated with the patient. In certain implementations, such a likelihood of fraud can be determined based on a degree of comparability between the one or more patient cluster classifications of the identified one or more of the one or more other patients and the patient cluster classification of the patient (as can be determined, for example, based on the comparison at 216). Additionally, in certain implementations, the referenced determining can be performed (such as in an automated or automatic fashion) with respect to one or more medical entity records and/or for one or more patients that are associated with one or more of the one or more claims that are associated with the medical entity.

At 220, processor 110 executing one or more of software modules 130, including, in certain implementations, fraud identification application 170, configures computing device 105 to provide one or more notifications. Such notifications can be provided, for example, with respect to the medical entity record. Additionally, such notifications can be provided based on one or more patient clusters, such as those identified at 212. Moreover, such notifications can reflect a determination of a likelihood of fraud, such as with respect to one or more claims, such as determined at 218. In certain implementations, the referenced providing can be performed (such as in an automated or automatic fashion) with respect to one or more medical entity records.

At 222, processor 110 executing one or more of software modules 130, including, in certain implementations, fraud identification application 170, configures computing device 105 to identify one or more claims associated with a provider. In certain implementations, such claims can be associated with one or more patients, and such patients can be associated with one or more respective patient variables. Additionally, in certain implementations, the referenced identifying can be performed (such as in an automated or automatic fashion) with respect to one or more medical entity records and/or for one or more providers that are associated with one or more of the one or more claims that are associated with the medical entity.

At 224, processor 110 executing one or more of software modules 130, including, in certain implementations, fraud identification application 170, configures computing device 105 to process one or more of patient variables, such as those associated with at least one of the one or more patients that are associated with at least one of the one or more claims that are associated with the provider. In doing so, one or more aggregate variables can be computed, such as for the provider. Moreover, in certain implementations, the referenced processing can be performed (such as in an automated or automatic fashion) with respect to one or more medical entity records and/or for one or more providers that are associated with one or more of the one or more claims that are associated with the medical entity.]

Examples of the referenced aggregate variables, such as for the provider, can include, but are not limited to: a Most Recent Patient Variable Set, a Patient Look forward Variable Set, and a Patient Look backward Variable Set. The aggregate variables can be statistics calculated over a group of patients, over any number of time periods, and can include minimum, maximum, range, mean, average and/or standard deviation for any/each of the variables. Also a number of providers (e.g., a threshold for a number of doctors over a period of time) can be implemented as well. Further examples of such aggregate variables include, but are not limited to: Standard deviation/mean for Rx Persistency by drug and drug class in look forward and look back time periods, Rx Persistency range in look forward and look back period, Standard deviation/mean for Rx billing time span in look back period, Standard deviation/mean for # of Rxs by drug and drug class, Standard deviation/mean for time difference calculations for Most Recent time period, Standard deviation/mean for Most Recent time period geographic location difference, Standard deviation/mean for Rx to Mx ratio, Standard deviation/mean for difference between projected cost based on Rx in isolation; and Rx along with Mx Percentage of patients that have claims by just one physician in total, Percentage of patients that have claims in more than 10 states, Percentage of patients that have claims by more than 20 physicians, Percentage of patients who have no prior claim; so have no Most Recent variable calculations, etc. Moreover, while some variables can have numeric values or other such attributes, others can be binary (e.g., yes/no). Further examples of provider variables include: Percentage of same medical procedures for Most Recent time period, Percentage of same medical procedure class for Most Recent time period, Percentage of same Rx drug for Most Recent time period, Percentage of same Rx drug class for Most Recent time period, Percentage of patient cash payment for Look back and Look forward time periods. Other such and related provider variables can include: DEA number, Practice geographic location, Practice demographic census information such as average age, income level and race, Name, Specialty, Number of patients who have an Rx claim from this physician, Number of patients who have Rx claims but no Mx claims, Number of patients who have an Mx claim from this physician, and Total number of other physicians his patient set has claims from. Further such examples include: Percentage of same medical procedures for Most Recent time period, Percentage of same medical procedure class for Most Recent time period, Percentage of same Rx drug for Most Recent time period, Percentage of same Rx drug class for Most Recent time period, Percentage of patient cash payment for Look back and Look forward time periods, Standard deviation/mean for Rx Persistency by drug and drug class in look forward and look back time periods, Rx Persistency range in look forward and look back period, Standard deviation/mean for Rx billing time span in look back period, Standard deviation/mean for # of Rxs by drug and drug class, Standard deviation/mean for time difference calculations for Most Recent time period, Standard deviation/mean for Most Recent time period geographic location difference, Standard deviation/mean for Rx to Mx ratio, Standard deviation/mean for difference between projected cost based on Rx in isolation; and Rx along with Mx, Percentage of patients that have claims by just one physician in total, Percentage of patients that have claims in more than 10 states, Percentage of patients that have claims by more than 20 physicians, Percentage of patients who have no prior claim; so have no Most Recent variable calculations Medical Entity xyz geographic location, Medical Entity xyz demographic census information such as average age, income level and race, Name, Specialty, Number of patients who have an Rx claim from medical entity, Number of patients who have Rx claims but no Mx claims from medical entity xyz, Number of patients who have an Mx claim for medical entity xyz, Total number of other medical entities it's patient set has claims to, Percentage of physicians who have high "closeness" factor.

At 226, processor 110 executing one or more of software modules 130, including, in certain implementations, fraud identification application 170, configures computing device 105 to process one or more aggregate variables (such as those respective aggregate variables computed at 224). In doing so, one or more provider clusters can be identified, using any number of clustering techniques are known to those of ordinary skill in the art. In certain implementations, such provider clusters can include one or more providers having one or more substantially similar aggregate variables (such as those computed at 224). Additionally, in certain implementations, the referenced processing can be performed (such as in an automated or automatic fashion) with respect to one or more medical entity records and/or for one or more providers that are associated with one or more of the one or more claims that are associated with the medical entity.

At 228, processor 110 executing one or more of software modules 130, including, in certain implementations, fraud identification application 170, configures computing device 105 to compute a provider cluster classification, such as with respect to the provider. Such a cluster classification can reflect the manner in which such clustering occurs, e.g., with respect to which of the various variables do the various providers cluster. For example, such as provider cluster classification can be computed based on one or more provider clusters, such as those identified at 226. In certain implementations, the referenced computing can be performed (such as in an automated or automatic fashion) with respect to one or more medical entity records and/or for one or more providers that are associated with one or more of the one or more claims that are associated with the medical entity.

At 230, processor 110 executing one or more of software modules 130, including, in certain implementations, fraud identification application 170, configures computing device 105 to compare a provider cluster classification (such as that computed at 228) of a provider with one or more provider cluster classifications of one or more other providers. In doing so, one or more of the one or more other providers that have a comparable provider cluster classification to the provider can be identified. In certain implementations, the referenced comparing can be performed (such as in an automated or automatic fashion) with respect to one or more medical entity records and/or for one or more providers that are associated with one or more of the one or more claims that are associated with the medical entity.

At 232, processor 110 executing one or more of software modules 130, including, in certain implementations, fraud identification application 170, configures computing device 105 to determine a likelihood of fraud with respect to one or more claims. In certain implementations, such a likelihood of fraud can be computed and/or expressed as a numeric value, (e.g., a scale from 1-10) reflecting the likelihood that a particular claim (or provider, or medical entity) is fraudulent. In certain implementations, such a likelihood of fraud can be determined with respect to one or more claims associated with the provider. Moreover, such a likelihood of fraud can be determined based on a degree of comparability (as determined based on the comparison at 230) between one or more provider cluster classifications (such as those computed at 228) of the identified one or more of the one or more other providers and the provider cluster classification of the provider. Additionally, in certain implementations, the referenced comparing can be performed (such as in an automated or automatic fashion) with respect to one or more medical entity records and/or for one or more providers that are associated with one or more of the one or more claims that are associated with the medical entity.

At 234, processor 110 executing one or more of software modules 130, including, in certain implementations, fraud identification application 170, configures computing device 105 to provide one or more notifications. In certain implementations, such notifications can be provided based on one or more identified provider clusters, such as those identified at 226. Additionally, such notifications can be provided based on one or more patient clusters, such as those identified at 212. In certain implementations, the referenced providing can be performed (such as in an automated or automatic fashion) with respect to one or more medical entity records.

At 236, processor 110 executing one or more of software modules 130, including, in certain implementations, fraud identification application 170, configures computing device 105 to compute one or more aggregate medical entity variables, substantially in the manner described in detail herein. In certain implementations, such aggregate medical entity variables can be computed with respect to one or more medical entity record(s). Moreover, such aggregate medical entity variables can be computed based on one or more identified patient clusters (such as those identified at 212), and/or based on one or more identified provider clusters (such as those identified at 226).

At 238, processor 110 executing one or more of software modules 130, including, in certain implementations, fraud identification application 170, configures computing device 105 to compare one or more aggregate medical entity variables, such as one or more aggregate medical entity variables associated with various respective medical entities.

At 240, processor 110 executing one or more of software modules 130, including, in certain implementations, fraud identification application 170, configures computing device 105 to provide one or more notifications. In certain implementations, such notifications can be provided with respect to at least one of the medical entities. Moreover, in certain implementations, such notifications can be provided based on a comparison of respective aggregate medical entity variables, such as at 238. Additionally, it should be noted that any/all of the notifications described as being provided herein can be provided based on the magnitude (e.g., the monetary amount) of the various underlying claims. Thus, for example, a notification can be provided in a scenario with a relatively lower likelihood of fraud where the claim amount is relatively large, while a notification need not necessarily be provided in a scenario with a relatively higher likelihood of fraud where the claim amount is relatively small.

At this juncture, it should be noted that although much of the foregoing description has been directed to systems and methods for fraud identification, the systems and methods disclosed herein can be similarly deployed and/or implemented in scenarios, situations, and settings far beyond the illustrated scenarios. It can be readily appreciated that fraud identification system 100 can be effectively employed in practically any scenario where any/all of the operation described herein can be useful. It should be further understood that any such implementation(s) and/or deployment(s) are within the scope of the systems and methods described herein.

It is to be understood that like numerals in the drawings represent like elements through the several figures, and that not all components and/or steps described and illustrated with reference to the figures are required for all embodiments or arrangements. It should also be understood that the embodiments, implementations, and/or arrangements of the systems and methods disclosed herein can be incorporated as a software algorithm, application, program, module, or code residing in hardware, firmware and/or on a computer useable medium (including software modules and browser plug-ins) that can be executed in a processor of a computer system or a computing device to configure the processor and/or other elements to perform the functions and/or operations described herein. It should be appreciated that according to at least one embodiment, one or more computer programs, modules, and/or applications that when executed perform methods of the present invention need not reside on a single computer or processor, but can be distributed in a modular fashion amongst a number of different computers or processors to implement various aspects of the systems and methods disclosed herein.

Thus, illustrative embodiments and arrangements of the present systems and methods provide a computer implemented method, computer system, and computer program product for fraud identification. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

What is claimed is:

1. A method comprising:
for each medical entity record received from a first device within a social network, the medical entity record comprising a set of one or more claims associated with a medical entity, each of the one or more claims being received from a first device via a network interface and associated with (a) a particular patient, (b) a particular provider, and (c) a particular date:
for each provider associated with at least one of the one or more claims stored in a database and associated with the medical entity:
identifying, by one or more processors of a second device, one or more claims stored in the database that are associated with the provider, each of the one or more claims being associated with one or more patients, each of the or more patients being associated with one or more respective patient variables that are stored in a patient profile received from a second device via the network interface and created based on episode of care attributes associated with the user,
processing, by the one or more processors, the one or more of the patient variables associated with at least one of the one or more patients that are associated with at least one of the one or more claims that are associated with the provider to automatically compute one or more aggregate variables for the provider;

using one or more machine learning techniques, processing, by the one or more processors, the respective one or more aggregate variables to identify one or more provider clusters, each of the one or more provider clusters comprising one or more providers having one or more substantially similar aggregate variables;

for each provider associated with at least one of the one or more claims associated with the medical entity:

computing, by the one or more processors and based on the one or more identified provider clusters, a provider cluster classification with respect to the provider, the provider cluster classification reflecting a manner in which the one or more aggregate variables based upon which the one or more identified provider clusters were identified, cluster with respect to one another;

comparing, by the one or more processors, the provider cluster classification of the provider with one or more provider cluster classifications of one or more other providers to identify one or more of the one or more other providers whose respective aggregate variables based upon which respective provider clusters were identified, cluster in the same manner as do the one or more aggregate variables associated with the provider; and determining, by the one or more processors, a closeness score, wherein a lower closeness score reflects (a) a greater degree of closeness between the one or more provider cluster classifications of the identified one or more of the one or more other providers and the provider cluster classification of the provider and (b) a greater degree of suspiciousness of an incidence of fraud with respect to one or more claims, as stored in the database and associated with the provider;

ordering, by the one or more processors, a plurality of medical entity records in accordance with their respective closeness scores;

automatically determining, by the one or more processors and with respect to at least one of the plurality of medical entity records and in view of (a) a greater degree of suspiciousness as reflected by a lower closeness score and (b) a monetary amount reflecting a high return on investment, that a suspicion of fraud should be investigated;

in response to the determination that the suspicion of fraud should be investigated, transmitting an instruction to perform one or more operations at a third device; and executing an application to automatically perform the one or more operations at the third device.

2. The method of claim 1, further comprising:

for each patient associated with at least one of the one or more claims associated with the medical entity:

identifying one or more claims associated with the patient, each of the one or more claims being associated with (a) a particular provider and (b) a particular date, selecting, from the one or more claims associated with the patient, at least (a) a first claim and (b) a second claim, each of the first claim and the second claim having one or more respective patient claim parameters, comparing one or more patient claim parameters of the first claim with one or more patient claim parameters of the second claim, and determining, based on the comparing, the one or more patient variables, the one or more patient variables reflecting one or more aspects of the one or more claims associated with the patient;

processing the respective determined patient variables to identify one or more patient clusters, each of the one or more patient clusters comprising one or more claims having one or more substantially similar patient variables; and providing, based on the one or more identified patient clusters, one or more notifications with respect to the medical entity record.

3. The method of claim 2, wherein the first claim and the second claim are associated with time intervals that are both chronologically distinct and chronologically contiguous to one another.

4. The method of claim 2, wherein the first claim comprises a medical claim and the second claim comprises a pharmaceutical claim.

5. The method of claim 2, wherein identifying one or more claims comprises identifying one or more claims associated with the patient that occur within a defined timeframe.

6. The method of claim 5, further comprising: for each medical entity record, automatically repeating the identifying one or more claims associated with the patient, selecting, comparing one or more patient claim parameters, and determining one or more patient variables for each of a plurality of defined timeframes for each patient associated with at least one of the one or more claims associated with the medical entity.

7. The method of claim 2, further comprising: for each medical entity record, for each patient associated with at least one of the one or more claims associated with the medical entity, computing, based on the one or more identified patient clusters, a patient cluster classification with respect to the patient, comparing the patient cluster classification of the patient with one or more patient cluster classifications of one or more other patients to identify one or more of the one or more other patients that have a comparable patient cluster classification to the patient; and determining, based on a degree of comparability between the one or more patient cluster classifications of the identified one or more of the one or more other patients and the patient cluster classification of the patient, a likelihood of fraud with respect to one or more claims associated with the patient.

8. The method of claim 2, further comprising:

for each medical entity record, computing, based on the one or more identified patient clusters, one or more aggregate medical entity variables;

comparing respective aggregate medical entity variables across the one or more medical entities; and providing, based on the comparison of respective aggregate medical entity variables, one or more notifications with respect to at least one of the medical entities.

9. The method of claim 1, wherein the closeness comprises one or more comparable time intervals occurring in between (1) claim submissions that are both (a) associated with the identified one or more of the one or more other providers and (b) associated with at least one of the one or more patients, and (2) claim submissions that are both (a) associated with the provider and (b) associated with the at least one of the one or more patients.

10. A system comprising:

a memory; and one or more processors coupled to the memory and to:

for each medical entity record received from a first device within a social network, the medical entity record comprising a set of one or more claims associated with a medical entity, each of the one or more claims being received from a first device via a network interface and associated with (a) a particular patient, (b) a particular provider, and (c) a particular date:

for each provider associated with at least one of the one or more claims stored in a database and associated with the medical entity:

identify one or more claims associated with the provider, each of the one or more claims being associated with one or more patients, each of the or more patients being associated with one or more respective patient variables that are stored in a patient profile received from a second device via the network interface and created based on episode of care attributes associated with the user, process the one or more of the patient variables associated with at least one of the one or more patients that are associated with at least one of the one or more claims that are associated with the provider to automatically compute one or more aggregate variables for the provider;

using one or more machine learning techniques, process the respective one or more aggregate variables to identify one or more provider clusters, each of the one or more provider clusters comprising one or more providers having one or more substantially similar aggregate variables;

for each provider associated with at least one of the one or more claims associated with the medical entity:

compute, based on the one or more identified provider clusters, a provider cluster classification with respect to the provider, the provider cluster classification reflecting a manner in which the one or more aggregate variables based upon which the one or more identified provider clusters were identified, cluster with respect to one another;

compare the provider cluster classification of the provider with one or more provider cluster classifications of one or more other providers to identify one or more of the one or more other providers whose respective aggregate variables based upon which respective provider clusters were identified, cluster in the same manner as do the one or more aggregate variables associated with the provider; and determine a closeness score, wherein a lower closeness score reflects (a) a greater degree of closeness between the one or more provider cluster classifications of the identified one or more of the one or more other providers and the provider cluster classification of the provider and (b) a greater degree of suspiciousness of an incidence of fraud with respect to one or more claims, as stored in the database and associated with the provider, wherein operation of the one or more processors is improved with respect to determining the closeness score based on the one or more claims associated with the medical entity as stored in the database;

order a plurality of medical entity records in accordance with their respective closeness scores;

automatically determine, with respect to at least one of the plurality of medical entity records and in view of (a) a greater degree of suspiciousness as reflected by a lower closeness score and (b) a monetary amount reflecting a high return on investment, that a suspicion of fraud should be investigated in response to the determination that the suspicion of fraud should be investigated, transmit an instruction to perform one or more operations at a third device; and execute a viewer to automatically perform the one or more operations at the third device.

11. The system of claim 10, wherein the one or more processors are further configured to:

for each patient associated with at least one of the one or more claims associated with the medical entity:

identify one or more claims associated with the patient, each of the one or more claims being associated with (a) a particular provider and (b) a particular date, select from the one or more claims associated with the patient, at least (a) a first claim and (b) a second claim, each of the first claim and the second claim having one or more respective patient claim parameters, compare one or more patient claim parameters of the first claim with one or more patient claim parameters of the second claim, and determine based on the comparing, the one or more patient variables, the one or more patient variables reflecting one or more aspects of the one or more claims associated with the patient;

process the respective determined patient variables to identify one or more patient clusters, each of the one or more patient clusters comprising one or more claims having one or more substantially similar patient variables; and provide, based on the one or more identified patient clusters, one or more notifications with respect to the medical entity record.

12. The system of claim 11, wherein the first claim and the second claim are chronologically contiguous to one another.

13. The system of claim 11, wherein the first claim comprises a medical claim and the second claim comprises a pharmaceutical claim.

14. The system of claim 11, wherein to identify one or more claims is to identify one or more claims associated with the patient that occur within a defined timeframe.

15. The system of claim 14, wherein the one or more processors are further to: for each medical entity record, repeat the identifying one or more claims associated with the patient, selecting, comparing one or more patient claim parameters, and determining one or more patient variables for each of a plurality of defined timeframes for each patient associated with at least one of the one or more claims associated with the medical entity.

16. The system of claim 11, wherein the one or more processors are further to:

for each medical entity record, for each patient associated with at least one of the one or more claims associated with the medical entity, compute based on the one or more identified patient clusters, a patient cluster classification with respect to the patient, compare the patient cluster classification of the patient with one or more patient cluster classifications of one or more other patients to identify one or more of the one or more other patients that have a comparable patient cluster classification to the patient; and determine based on a degree of comparability between the one or more patient cluster classifications of the identified one or more of the one or more other patients and the patient cluster classification of the patient, a likelihood of fraud with respect to one or more claims associated with the patient.

17. The system of claim 11, wherein the one or more processors are further to:
for each medical entity record, compute based on the one or more identified patient clusters, one or more aggregate medical entity variables;
compare respective aggregate medical entity variables across the one or more medical entities; and
provide based on the comparison of respective aggregate medical entity variables, one or more notifications with respect to at least one of the medical entities.

18. The system of claim 10, wherein the closeness comprises one or more identical time intervals that occur in between (1) claim submissions that are both (a) associated with the identified one or more of the one or more other providers and (b) associated with at least one of the one or more patients, and (2) claim submissions that are both (a) associated with the provider and (b) associated with the at least one of the one or more patients.

19. A non-transitory computer storage medium encoded with instructions that when executed by one or more data processing apparatus cause the one or more data processing apparatus to perform operations comprising:
for each medical entity record received from a first device within a social network, the medical entity record comprising a set of one or more claims stored in a database and associated with a medical entity, each of the one or more claims being received from a first device via a network interface and associated with (a) a particular patient, (b) a particular provider, and (c) a particular date:
for each provider associated with at least one of the one or more claims associated with the medical entity:
identifying one or more claims associated with the provider, each of the one or more claims being associated with one or more patients, each of the or more patients being associated with one or more respective patient variables that are stored in a patient profile received from a second device via the network interface and created based on episode of care attributes associated with the user,
processing the one or more of the patient variables associated with at least one of the one or more patients that are associated with at least one of the one or more claims that are associated with the provider to automatically compute one or more aggregate variables for the provider;
using one or more machine learning techniques, processing the respective one or more aggregate variables to identify one or more provider clusters, each of the one or more provider clusters comprising one or more providers having one or more substantially similar aggregate variables;
for each provider associated with at least one of the one or more claims associated with the medical entity:
computing, based on the one or more identified provider clusters, a provider cluster classification with respect to the provider, the provider cluster classification reflecting a manner in which the one or more aggregate variables based upon which the one or more identified provider clusters were identified, cluster with respect to one another;
comparing the provider cluster classification of the provider with one or more provider cluster classifications of one or more other providers to identify one or more of the one or more other providers whose respective aggregate variables based upon which respective provider clusters were identified, cluster in the same manner as do the one or more aggregate variables associated with the provider; and
determining a closeness score, wherein a lower closeness score reflects (a) a greater degree of closeness between the one or more provider cluster classifications of the identified one or more of the one or more other providers and the provider cluster classification of the provider and (b) a greater degree of suspiciousness of an incidence of fraud with respect to one or more claims associated with the provider, wherein operation of the one or more data processing apparatus is improved with respect to determining the closeness score based on the one or more claims associated with the medical entity as stored in the database;
ordering a plurality of medical entity records in accordance with their respective closeness scores;
automatically determining, with respect to at least one of the plurality of medical entity records and in view of (a) a greater degree of suspiciousness as reflected by a lower closeness score and (b) a monetary amount reflecting a high return on investment, that a suspicion of fraud should be investigated;
in response to the determination that the suspicion of fraud should be investigated, transmitting an instruction to perform one or more operations at a third device; and
executing an application to automatically performing the one or more operations at the third device, wherein to perform the one or more operations at the third device comprises configuring the third device to request data from a fourth device.

20. The non-transitory computer storage medium of claim 19, wherein the comparability comprises one or more identical time intervals occurring in between (1) claim submissions that are (a) associated with the identified one or more of the one or more other providers, (b) associated with at least one of the one or more patients, and (c) associated with one or more particular drugs and (2) claim submissions that are (a) associated with the provider and (b) associated with the at least one of the one or more patients, and (c) associated with the one or more particular drugs.

* * * * *